United States Patent [19]

Abramson

[11] 3,966,335
[45] June 29, 1976

[54] MULTI-DIGITAL SURGICAL SCRUB BRUSH

[76] Inventor: Daniel J. Abramson, 2800 Greenvale St., Chevy Chase, Md. 20015

[22] Filed: May 16, 1975

[21] Appl. No.: 578,009

[52] U.S. Cl. .............................. 401/10; 401/183; 401/196; 128/81 R
[51] Int. Cl.² ................. A46B 11/00; A46B 15/00
[58] Field of Search ............... 401/10, 183, 196; 15/244 B, 167 B; 128/81 R

[56] References Cited
UNITED STATES PATENTS

| | | | |
|---|---|---|---|
| 1,028,211 | 6/1912 | Heath | 15/167 B |
| 2,424,509 | 7/1947 | Singer | 15/97 R |
| 3,467,978 | 9/1969 | Golden | 15/111 |
| 3,611,468 | 10/1971 | Michael | 15/244 B X |
| 3,694,845 | 10/1972 | Engelsher | 15/244 C |
| 3,811,783 | 5/1974 | Johnson | 401/183 |
| 3,843,991 | 10/1974 | Vallis | 15/167 B |

*Primary Examiner*—Lawrence Charles
*Attorney, Agent, or Firm*—Alex Mazel

[57] ABSTRACT

A surgical scrub brush featuring four bristle-lined troughs or furrows or tubular apertures for rapid, efficient and simultaneous scrubbing of the four fingers, and also providing for the scrubbing of the hands, arms and web spaces, including both the outer and relatively inaccessible interdigital areas of the fingers and providing additionally an outer bristle surface and on the opposite surface a layer of foam rubber or plastic for general overall scrubbing of the hands, arms and thumbs, having additionally, rows of relatively short stiffer bristles and/or raised plastic edges on the other two sides for cleaning the finger tips, nails and under the nails.

12 Claims, 5 Drawing Figures

MULTI-DIGITAL SURGICAL SCRUB BRUSH

BACKGROUND OF THE INVENTION

It is accepted practice that surgeons must perform pre-operative scrubbing of their arms, hands and fingers to achieve as an aseptic condition thereof as possible in order to enhance the clinical safety of the patient under operative conditions, while the outer gross surfaces of the arms and hands are relatively more easily accessible, — the fingers and nails, particularly the interdigital surfaces and web spaces thereof are difficult to get at with the conventional square brush for proper scrubbing to attain asepsis, making the procedure, if not inadequate, then difficult and/or time consuming. The demand on a surgeon's time is great and although a surgeon will normally spend a specified time to insure a proper scrub, it is obvious that where an emergency is involved, a surgeon will need a thorough scrub in minimum time. Hitherto, it was mandatory for the surgeon to scrub all surfaces of each finger and each nail individually and separately with a conventional brush, and with relative difficulty as to the interdigital surfaces and web areas thereof. Further, bristles of a flexibility sufficient for use on the outer surfaces would not be stiff enough to clean under the nails.

SUMMARY OF THE INVENTION

The present invention provides for both rapid and efficient pre-operative scrubbing of the surgeon's arms, hands, fingers and nails. The most inaccessible and time consuming portion of the scrub, i.e., that of the interdigital finger surfaces and web spaces is now quickly, easily and aseptically performed by the brush of the invention which provides four aligned, relatively parallel, bristle lined troughs or furrows or enclosed bristle lined tubular apertures (to accommodate the four fingers) as depicted in the Figures. The invention also contemplates an outer bristle layer on the opposed surface. The combined different scrubbing effect of the bristles as well as that obtained from the foam layer leads to greater scrubbing efficiency and adaptability under conditions of use. There are also provided on the other two sides, two rows of short height, relatively stiff bristles, or, alternatively one row of stiff, short bristles on one side and a row of plastic edges or protrusions on the opposed side, for cleaning the finger tips, nails and under the nails. The source of the necessary soap/detergent/antiseptic composition may be included within the brush of the invention e.g. 1) by impregnation of the foam layer acting thereby as a sponge or 2) by providing a reservoir therein, e.g. a pressure collapsible tube within the brush, with outlets to the bristles and the foam layer. Although the brush of the invention may be re-cycled for further use after sterilization, it is contemplated that the brush will come packaged in a sealed sterile container, containing the scrubbing composition as desired, for disposal after a single usage. When the shape of the support base for the bristles is in the form of finger length troughs (wherein the four fingers can be placed therein by a vertical or horizontal motion) or in the form of four tubular apertures, it will be seen that this four finger arrangement serves also to provide a firm grip (together with the thumb) when the fingers are inserted, to enable the surgeon to effectively scrub the other hand and arm outer surfaces, without changing and without the slipping ordinarily occurring in a wet soapy medium. Thus, after the fingers on one hand are scrubbed simultaneously either with an up-and-down and/or a forward-and-back motion, the brush may then be gripped by the same fingers (and thumb applying gripping pressure) for scrubbing the other hand and arm with the outer bristles, foam layer and nail and finger tip bristles or plastic edges as described. The outstanding efficiency and potential time saving arrangement of the brush construction of the invention is thus made apparent. Also, the impregnated foam layer can be used for preparation of the wound and/or incision areas, for surgery employing the soap/detergent/antiseptic composition contained therein.

In the Figures, 1 is the support base, which can be of a suitable plastic, for anchoring the bristles, for supporting the foam layer 6 and where desired, the reservoir 4 for the soap/detergent/antiseptic solution having outlets 5. The bristles 2 project inwardly in the troughs and at the top of the vertical walls, the bristles are fan-shaped so as to project outwardly and inwardly at all angles, so as to scrub the fingers and also to provide the outer layer of bristles. Bristles from the vertical walls projecting inwardly are long enough to mesh with the bristles of the opposite wall to provide a finger-round brushing surface. The furrows, troughs and tunnels will, of course, be approximately finger length and may be tapered to accommodate the natural taper of the finger and/or the bristle length and stiffness be selected to insure adequate scrubbing of the finger surfaces. The finger tip and nail cleaning short, stiff bristles and/or plastic edges are represented by 3. The foam rubber or foam plastic layer is 6, which layer may be impregnated by the soap-detergent/antiseptic composition, where the reservoir is eliminated. The reservoir 4, as indicated above, can be pressure activated to force the composition through outlets 5 and conventionally activated with water to form a lather. The support base, foam layer and/or resevoir can be attached to each other by conventional mechanical or adhesive means.

Figure 2:
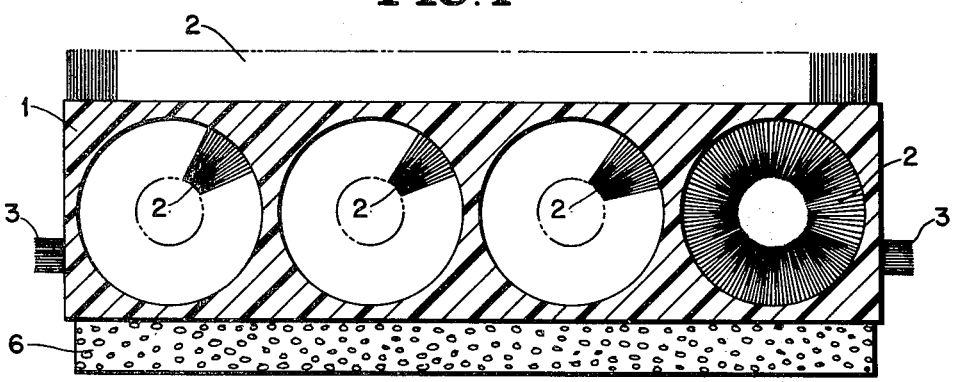
FIG. 2 shows a modification in which the finger scrubbers are enclosed tunnels with the bristles pointed inwardly around the circumference and wherein the fingers are scrubbed by a push-pull motion through the tunnels.
Figure 3:
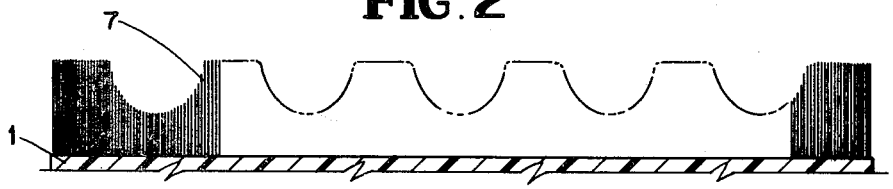
FIG. 3 shows the outer bristle layer as in 2 of FIG. 2 wherein the bristles are furrowed along the length of the brush to accommodate the fingers. In this variation, the fingers (as well as the hands and arms) may be scrubbed with the outer layer of bristles with the fingers being scrubbed upper and lower sides in turn. This outer layer reaches also the web spaces and interdigital areas. This furrowed outer layer will scrub regular and irregular skin surfaces.

In. FIG. 2, bristles 2 can be of the same length or they can take the form of the furrows of bristles 7 of FIG. 3 where the bristles are of differential length to form furrows along the outer brush surface.

Figure 1:
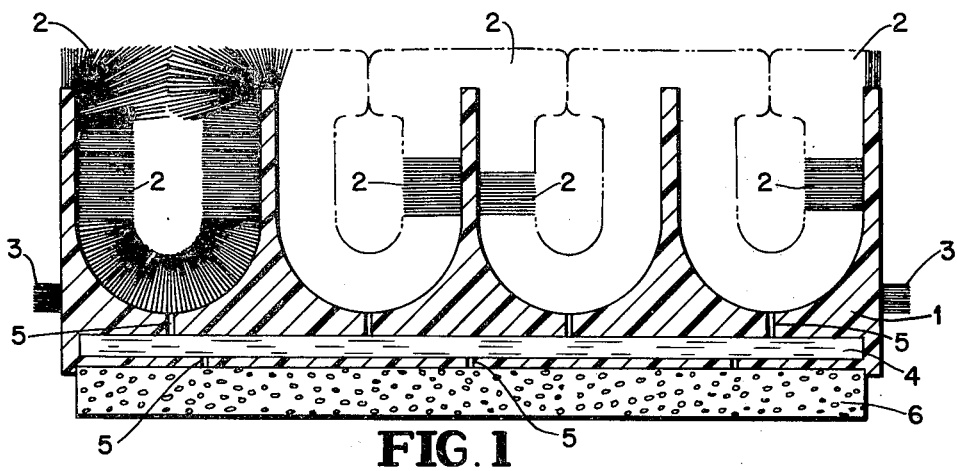
FIG. 1 shows a cross-section of a brush according to the invention in which the base or support in which the bristles are anchored has five vertical walls providing four troughs for the fingers, the distance between the walls being finger width plus that needed to accommodate the bristles extending into the spaces.

In FIG. 2, the reservoir 4 is not shown, but as in the brush of FIG. 1, it can be included or eliminated as desired, if foam layer 6 is impregnated, or the brush is packaged in the composition in a sealed container.

Figure 4:
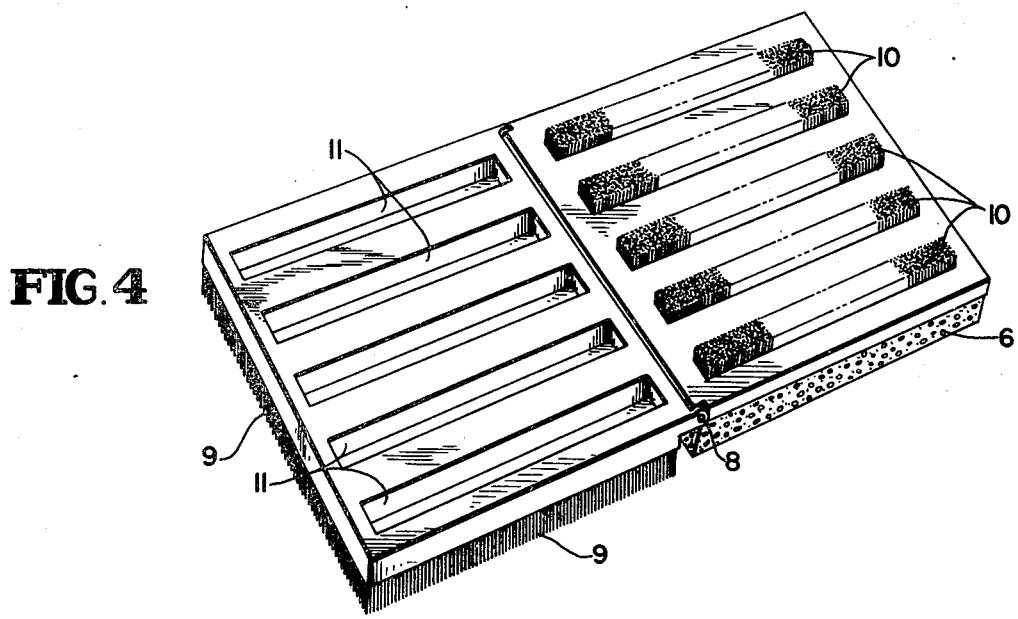
FIG. 4 shows a hinged version of the brush, opened flat, as depicted. When the brush is folded shut, the inside bristles will project through the matching openings and with the outside bristles form a bristle layer which can be straight or furrowed as desired, depending on the length of bristles 10. Or, the inside bristle spaced rows can be used to clean the fingers due to the furrow effect and when the brush is folded on the hinge, the combined bristle rows can be used as a bristle layer for scrubbing the arms, hands and thumbs, both gross and irregular surfaces thereof.
Figure 5:
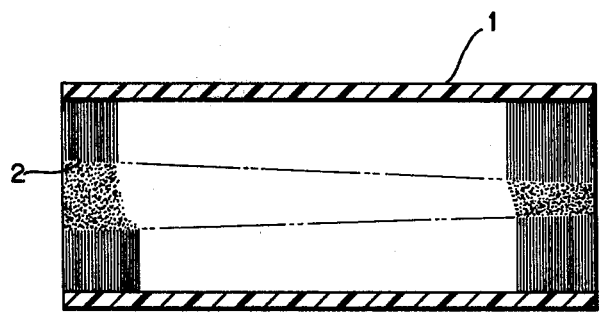
FIG. 5 represents a cross-sectional view of an optional tapering effect along the finger scrubbing means.

In FIG. 4, 6 is again the foam layer which may be impregnated with the composition, 10 represents five rows of bristles which pass through openings 11 to line up with the 6 rows of bristles 9, when the brush is folded shut on hinge 8. Thus, in the open position, the five rows of bristles 10 creating four troughs or furrows, where very short bristles, if desired, can be anchored in the hollows of the troughs can be used to scrub the fingers simultaneously. In the shut position, the bristles 10 protrude through longitudinal apertures 11 to line up alongside bristles 9, to create a brush face of similar height bristles or either 10 or 9 will be of different heights to create a brush face similar to 7. In FIG. 1, the fingers may be inserted downwardly into the troughs through bristles 2 and brushed with both an up-and-down motion and push-pull motion along the length of the troughs. Irregular arrangements of external bristles as in fan-shaped top of FIG. 1 and the differential length bristle, furrow effect of FIG. 3 enables efficient scrubbing of external irregular surfaces. The fan-shaped bristles covering the openings of the troughs in FIG. 1 by intermeshing will have an inherent differential length bristle effect for scrubbing the fingers as indicated above, or for use in scrubbing outer gross surfaces, skin irregularities and web spaces. The natural taper of the fingers may be accommodated by a taper along the length of the furrows, troughs or tunnels, or the bristle heights be adjusted to accommodate the fingers along the lengths thereof to insure adequate brush contact of all areas of the fingers.

THE INVENTION

As will be seen from the Figures and the discussion thereto and in the description above, the invention comprises a multidigital surgical scrub brush which is both remarkably efficient in providing the necessary degree of asepsis in a minimum of time, when employed by a surgeon for pre-operative scrubbing of the hands, arms, all surfaces of the fingers and web spaces, nails and under-the-nails areas. The brush of the invention solves the problem of proper yet rapid and simultaneous scrubbing of the fingers, particularly the interdigital surfaces and web spaces, hitherto relatively inaccessible and time consuming with the conventional square, uniform bristle surgical brush.

Another object of the invention is to avoid the laborious and possibly inadequate scrubbing of each and every finger surface and irregular skin surface. As can be seen the instant brush facilitates the simultaneous scrubbing of all areas of the four fingers. The brush of FIG. 1 not only provides for an in-and-out scrubbing motion axially along the length of the troughs but also by an up-and-down vertical motion through the fan-shaped intermeshed bristles at the top of each trough and those bristles projecting inwardly. Either motion, or preferably both will insure simultaneous, rapid and efficient scrubbing of all finger areas in an easy manner not hitherto possible.

Still another object of the invention is to provide a surgical scrub brush which will make possible a minimum scrub time to achieve acceptable asepsis, of extreme importance in the event of an emergency operation and of obvious benefit to the patient and the surgeon.

Still a further object of the invention is to provide a surgical scrub brush which will make possible a minimum scrub time to achieve acceptable asepsis, of extreme importance in the event of an emergency operation and of obvious benefit to the patient and the surgeon.

Still a further object of the invention is to provide a surgeon's scrub brush which permits a firm grip, in a slippery soap or detergent mixture. The bristle finger troughs or tunnels not only scrub the fingers simultaneously but provide a grip, with pressure from the thumb for scrubbing the other hand, arm, fingers, thumb and nails with the other parts of the brush as indicated above.

Still a further object is to provide a brush having means for cleaning and scrubbing of all areas of the hands, arms, nails and fingers, including the hitherto relatively inaccessible interdigital areas simultaneously, as well as the finger tips, nails and under nails areas. For the latter purposes, there are provided the narrower rows of shorter, stiffer bristles or one of these rows can be replaced with a row of raised, short plastic edges for getting under the finger nails for cleaning purposes. The brush also provides for an outer layer of bristles of uniform height or furrowed for cleaning gross outer sections of skin, irregular skin areas, web spaces, finger areas or the like and a layer of foam (synthetic resin or rubber) for a differential scrubbing effect, to insure overall scrubbing efficiency and for applying the detergent/soap/antiseptic solution to the wound and/or surgical operation skin area for cleansing and aseptic purposes.

As will be understood, the base in which the bristles are anchored, as to which the foam layer is attached (and reservoir where desired) can be of a suitable synthetic resin or plastic of which may types and kinds are available and suitable. Similarly, the bristles may be of natural origin, animal or vegetable, or of synthetic resin or plastic. The foam layer scrubbing surface may also be of a conventional sponge like material, e.g., rubber, foamed polyurethane, foamed polystyrene and the like. The cellular density thereof is selected so that the foamed layer provides adequate shape retaining properties and abrasiveness to perform desired scrubbing action and to retain the scrubbing composition when impregnated therewith as described above. Otherwise, a reservoir or tube, pressure activated, containing said composition may be situated between the foam layer and bristle base, with outlets thereto.

As will be seen from the above description and the Figures, the brush of the invention comprises novel features designed to (1) quickly, efficiently and simultaneously scrub all areas of the fingers, particularly the relatively inaccessible interdigital surfaces and web spaces, as well as the other regular and irregular surfaces of the hands, arms, fingers and nails (2) to provide for a unique construction which not only provides for the above, but also furnishes a firm grip between the fingers and the thumb when using the outer bristles, foam layer and finger (tips and nails) cleaning means on the other hand, arm, fingers and nails (3) to accomplish an acceptably aseptic pre-operative surgical scrub in a minimal time, particularly under emergency conditions, not hitherto attainable with a hand held surgical scrub brush (4) prepare the part to be operated on with the impregnated foam layer.

While the novel surgical scrub brush of the invention has been described above in several aspects and modifications, it is not intended that these serve to limit the invention thereto, since other obvious and equivalent modifications will occur to the ordinary skilled artisan which will not constitute departures from the spirit of the invention as disclosed herein and claimed below.

I claim:

1. A scrub brush comprising means for scrubbing all surfaces of the four fingers and web spaces simultaneously said means being in the form of four connected aligned finger length troughs which are bristle lined inwardly from all surfaces of the sides and bottoms, having fan shaped bristles projecting in all directions from the top of the trough walls so as to form an outer bristle surface as well as providing inwardly projecting bristles, intermeshing with the fan shaped bristles from the opposite trough wall to complete the bristle encirclement of each finger space, said intermeshed bristles being yieldable to a vertical brushing motion, as well as providing for a horizontal brushing motion, said scrub brush having attached to the opposite surface to the outer bristles surface, a plastic foam layer and on the other two opposed sides means for cleaning the nails, under the nails and the finger tips.

2. The brush of claim 1 in which the simultaneous four finger scrubbing means are tapered slightly axially in the direction of the finger tips.

3. The brush of claim 1 in which the foamed plastic layer is impregnated with a scrubbing composition.

4. The brush of claim 1 in which a scrubbing composition is contained in a pressure activated reservoir tube located between the foamed plastic layer and the bristle anchoring base and having outlets to the foam layer and through the base to the bristles.

5. The brush of claim 1 in which the outer bristle layer is of differential bristle length to provide a furrow effect.

6. The brush of claim 1 wherein one longitudinal side between the outer bristle surface and the foamed plastic layer bears a narrow row of short, relatively stiff bristles and the opposing side bears a row of thin discrete plastic edges of a thickness to fit under the finger nails.

7. A scrub brush comprising means for scrubbing all surfaces of the four fingers and web spaces simultaneously said means being in the form of four connected longitudinally aligned enclosed finger length tunnels, each tunnel having bristles projecting inwardly from all surfaces of the inner tubular walls throughout the length thereof, said brush having an outer brush surface and on the opposite side an attached layer of plastic foam, and on the two other opposed sides means for cleaning the nails, under the nails and finger tips.

8. The brush of claim 7 in which the simultaneous four fingered scrubbing means are tapered slightly axially in the direction of the finger tips.

9. The brush of claim 7 in which the plastic foam layer is impregnated with a scrubbing composition.

10. The brush of claim 7 in which a scrubbing composition is contained in a pressure activated reservoir tube located between the plastic foan layer and the bristle anchoring base and having outlets to the foam layer and through the base to the bristles.

11. The brush of claim 7 in which the outer bristle layer is of differential bristle length to provide a furrow effect.

12. The brush of claim 7 wherein one longitudinal side between the outer bristle surface and the plastic foam layer bears a narrow row of short, relatively stiff bristles and the opposing side bears a row of thin discrete plastic edges of a thickness to fit under the fingernails.

* * * * *